US009918832B2

(12) United States Patent
Tian et al.

(10) Patent No.: US 9,918,832 B2
(45) Date of Patent: *Mar. 20, 2018

(54) BIOLOGICAL TISSUE FOR SURGICAL IMPLANTATION

(75) Inventors: Bin Tian, Irvine, CA (US); Jim Davidson, San Juan Capistrano, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1242 days.

This patent is subject to a terminal disclaimer.

(21) Appl. No.: 13/189,036

(22) Filed: Jul. 22, 2011

(65) Prior Publication Data

US 2012/0012487 A1 Jan. 19, 2012

Related U.S. Application Data

(62) Division of application No. 11/877,548, filed on Oct. 23, 2007, now Pat. No. 8,007,992.

(60) Provisional application No. 60/854,938, filed on Oct. 27, 2006.

(51) Int. Cl.
*A61F 2/24* (2006.01)
*A61L 27/36* (2006.01)
*A61L 27/50* (2006.01)
*A01N 1/02* (2006.01)

(52) U.S. Cl.
CPC .......... *A61F 2/2415* (2013.01); *A01N 1/0215* (2013.01); *A61L 27/3604* (2013.01); *A61L 27/3687* (2013.01); *A61L 27/507* (2013.01); *A61L 2430/40* (2013.01)

(58) Field of Classification Search
CPC ... A61F 2/2412; A61F 2/2415; A01N 1/0215; A61L 2430/40; A61L 27/3604; A61L 27/3687; A61L 27/507; G06F 2203/04806; G06F 2203/04808; G06F 3/04817; G06F 3/0488; G06F 3/04886
USPC ...................................................... 623/2.13
See application file for complete search history.

(56) References Cited

U.S. PATENT DOCUMENTS

| 2,393,580 | A | 1/1946 | Weiskopf |
|---|---|---|---|
| 2,484,813 | A | 10/1949 | Bower |
| 2,567,929 | A | 9/1951 | Fessenden |
| 3,002,895 | A | 10/1961 | Freedman |
| 3,093,439 | A | 6/1963 | Bothwell |
| 3,818,894 | A | 6/1974 | Wichterle et al. |
| 3,870,789 | A | 3/1975 | Mikat |
| 3,927,422 | A | 12/1975 | Sawyer |
| 3,961,097 | A | 6/1976 | Gravlee, Jr. |
| 3,966,401 | A | 6/1976 | Hancock et al. |
| 4,050,893 | A | 9/1977 | Hancock et al. |
| 4,067,091 | A | 1/1978 | Backman |
| 4,082,507 | A | 4/1978 | Sawyer |
| 4,120,649 | A | 10/1978 | Schechter |
| 4,120,991 | A | 10/1978 | Ornstein et al. |
| 4,197,658 | A | 4/1980 | Fraser |
| 4,206,844 | A | 6/1980 | Thukamoto et al. |
| 4,207,689 | A | 6/1980 | Romera-Sierra et al. |
| 4,224,992 | A | 9/1980 | Comberiati et al. |
| 4,294,753 | A | 10/1981 | Urist |
| 4,320,157 | A | 3/1982 | von Hagens |
| 4,323,358 | A | 4/1982 | Lentz et al. |
| 4,328,256 | A | 5/1982 | Romero-Sierra et al. |
| 4,347,671 | A | 9/1982 | Dias et al. |
| 4,350,492 | A | 9/1982 | Wright et al. |
| 4,357,274 | A | 11/1982 | Werner |
| 4,372,743 | A | 2/1983 | Lane |
| 4,378,224 | A | 3/1983 | Nimni et al. |
| 4,402,697 | A | 9/1983 | Pollock et al. |
| 4,405,327 | A | 9/1983 | Pollock |
| 4,481,009 | A | 11/1984 | Nashef |
| 4,553,974 | A | 11/1985 | Dewanjee |
| 4,599,084 | A | 7/1986 | Nashef |
| 4,624,822 | A | 11/1986 | Arru et al. |
| 4,647,283 | A | 3/1987 | Carpentier et al. |
| 4,648,881 | A | 3/1987 | Carpentier et al. |
| 4,655,773 | A | 4/1987 | Grassi |
| 4,676,070 | A | 6/1987 | Linner |
| 4,729,139 | A | 3/1988 | Nashef |
| 4,729,766 | A | 3/1988 | Bergentz et al. |
| 4,753,652 | A | 6/1988 | Langer et al. |
| 4,758,151 | A | 7/1988 | Arru et al. |

(Continued)

FOREIGN PATENT DOCUMENTS

EP 0169259 1/1986
EP 0169259 A1 1/1986

(Continued)

OTHER PUBLICATIONS

Vesley, I. (2005) Heart Valve Tissue Engineering. Circulation Research 97(8): 743-55.*
Al-Fagih, et al., "Aortic Valve Repair Using Bovine Pericardium for Cusp Extension," J. Thor. Cardiov. Surg. 96 (5): 760-764 (1988), abstract only.
Chanda, J., et al., "Heparin in Calcification Prevention of Porcine Pericardial Bioprostheses," Biomaterials, Elsevier Science Publishers, vol. 18, No. 16, ISSN: 0142-9612, Aug. 1, 1997.
Chvapil, et al., "Use of Chemically Purified and Cross-Linked Bovine Pericardium as a Ligament Substitute," J. Biomed. Mat. Res. 21 (12): 1383-1394 (1987), abstract only.

(Continued)

Primary Examiner — Lisa J Hobbs
(74) Attorney, Agent, or Firm — Lee-Ann Smith-Freeman; Michelle C. Kim; Pui Tong Ho

(57) ABSTRACT

A method of treating a biological tissue that enables dry storage of said tissue is disclosed. In one embodiment, the method comprises contacting the biological tissue with a non-aqueous treatment solution comprising a polyhydric alcohol and a $C_1$-$C_3$ alcohol and removing a portion of the treatment solution from the solution-treated biological tissue. Also disclosed is biological tissue prepared using the above process and prosthetic devices made with such tissue.

6 Claims, No Drawings

(56) References Cited

U.S. PATENT DOCUMENTS

| | | |
|---|---|---|
| 4,770,665 A | 9/1988 | Nashef |
| 4,776,853 A | 10/1988 | Klement et al. |
| 4,786,287 A | 11/1988 | Nashef et al. |
| 4,793,344 A | 12/1988 | Cumming et al. |
| 4,800,603 A | 1/1989 | Jaffe |
| 4,831,065 A | 5/1989 | Pietsch et al. |
| 4,838,888 A | 6/1989 | Nashef |
| 4,865,871 A | 9/1989 | Livesey et al. |
| 4,885,005 A | 12/1989 | Nashef et al. |
| 4,891,319 A | 1/1990 | Roser |
| 4,911,713 A | 3/1990 | Sauvage et al. |
| 4,958,008 A | 9/1990 | Petite et al. |
| 4,969,912 A | 11/1990 | Kelman et al. |
| 4,975,526 A | 12/1990 | Kuberasampath et al. |
| 4,976,733 A | 12/1990 | Giradot |
| 4,990,131 A | 2/1991 | Dardik et al. |
| 4,994,030 A | 2/1991 | Glowczewskie, Jr. et al. |
| 4,994,237 A | 2/1991 | Login et al. |
| 4,996,054 A | 2/1991 | Pietsch et al. |
| 5,002,566 A | 3/1991 | Carpentier et al. |
| 5,011,494 A | 4/1991 | von Recum et al. |
| 5,011,913 A | 4/1991 | Benedict et al. |
| 5,024,830 A | 6/1991 | Linner |
| 5,044,165 A | 9/1991 | Linner et al. |
| 5,051,401 A | 9/1991 | Sikes |
| 5,068,086 A | 11/1991 | Sklenak et al. |
| 5,068,100 A | 11/1991 | McClanahan |
| 5,080,670 A | 1/1992 | Imamura et al. |
| 5,094,661 A | 3/1992 | Levy et al. |
| 5,104,405 A | 4/1992 | Nimni |
| 5,108,923 A | 4/1992 | Benedict et al. |
| 5,116,564 A | 5/1992 | Jansen et al. |
| 5,131,908 A | 7/1992 | Dardik et al. |
| 5,147,514 A | 9/1992 | Mechanic |
| 5,149,621 A | 9/1992 | McNally et al. |
| 5,149,653 A | 9/1992 | Roser |
| 5,154,007 A | 10/1992 | Piunno et al. |
| 5,163,955 A | 11/1992 | Love et al. |
| 5,200,399 A | 4/1993 | Wettlaufer et al. |
| 5,215,541 A | 6/1993 | Nashef et al. |
| 5,275,954 A | 1/1994 | Wolfinbarger et al. |
| 5,279,612 A | 1/1994 | Eberhardt |
| 5,288,288 A | 2/1994 | Lewis et al. |
| 5,290,558 A | 3/1994 | O'Leary et al. |
| 5,292,802 A | 3/1994 | Rhee et al. |
| 5,296,583 A | 3/1994 | Levy |
| 5,298,254 A | 3/1994 | Prewett et al. |
| 5,329,846 A | 7/1994 | Bonutti |
| 5,332,475 A | 7/1994 | Mechanic |
| 5,336,616 A | 8/1994 | Livesey et al. |
| 5,368,608 A | 11/1994 | Levy et al. |
| 5,397,353 A | 3/1995 | Oliver et al. |
| 5,424,047 A | 6/1995 | Zwingenberger et al. |
| 5,436,291 A | 7/1995 | Levy et al. |
| 5,437,287 A | 8/1995 | Phillips et al. |
| 5,447,536 A | 9/1995 | Giradot et al. |
| 5,447,724 A | 9/1995 | Helmus et al. |
| 5,460,962 A | 10/1995 | Kemp |
| 5,476,516 A | 12/1995 | Seifter et al. |
| 5,507,813 A | 4/1996 | Dowd et al. |
| 5,509,932 A | 4/1996 | Keogh et al. |
| 5,554,184 A | 9/1996 | Machiraju |
| 5,556,379 A | 9/1996 | Wolfinbarger |
| 5,558,875 A | 9/1996 | Wang |
| 5,595,571 A | 1/1997 | Jaffe et al. |
| 5,613,982 A | 3/1997 | Goldstein |
| 5,632,778 A | 5/1997 | Goldstein |
| 5,645,587 A | 7/1997 | Chanda et al. |
| 5,674,298 A | 10/1997 | Levy et al. |
| 5,679,112 A | 10/1997 | Levy et al. |
| 5,695,820 A | 12/1997 | Davis et al. |
| 5,697,972 A | 12/1997 | Kim et al. |
| 5,713,953 A | 2/1998 | Vallana et al. |
| 5,716,399 A | 2/1998 | Love |
| 5,720,777 A | 2/1998 | Jaffe et al. |
| 5,720,894 A | 2/1998 | Neev et al. |
| 5,733,339 A | 3/1998 | Giradot et al. |
| 5,746,775 A | 5/1998 | Levy et al. |
| 5,762,600 A | 6/1998 | Bruchman et al. |
| 5,766,520 A | 6/1998 | Bronshtein |
| 5,769,780 A | 6/1998 | Hata et al. |
| 5,770,193 A | 6/1998 | Vacanti et al. |
| 5,773,285 A | 6/1998 | Park |
| 5,776,182 A | 7/1998 | Bruchman et al. |
| 5,782,914 A | 7/1998 | Schankereli |
| 5,782,915 A | 7/1998 | Stone |
| 5,782,931 A | 7/1998 | Yang et al. |
| 5,792,603 A | 8/1998 | Dunkelman et al. |
| 5,843,180 A | 12/1998 | Jaffe et al. |
| 5,843,181 A | 12/1998 | Jaffe et al. |
| 5,843,182 A | 12/1998 | Goldstein |
| 5,855,620 A | 1/1999 | Bishopric et al. |
| 5,856,102 A | 1/1999 | Bierke-Nelson et al. |
| 5,856,172 A | 1/1999 | Greenwood et al. |
| 5,862,806 A | 1/1999 | Cheung |
| 5,865,849 A | 2/1999 | Stone |
| 5,873,812 A | 2/1999 | Ciana et al. |
| 5,879,383 A | 3/1999 | Bruchman et al. |
| 5,882,850 A | 3/1999 | Khor et al. |
| 5,882,918 A | 3/1999 | Goffe |
| 5,899,936 A | 5/1999 | Goldstein |
| 5,902,338 A | 5/1999 | Stone |
| 5,904,718 A | 5/1999 | Jeffries |
| 5,911,951 A | 6/1999 | Giradot et al. |
| 5,913,900 A | 6/1999 | Stone |
| 5,919,472 A | 7/1999 | Trescony et al. |
| 5,921,980 A | 7/1999 | Kim |
| 5,922,027 A | 7/1999 | Stone |
| 5,928,281 A | 7/1999 | Huynh et al. |
| 5,931,969 A | 8/1999 | Carpentier et al. |
| 5,935,168 A | 8/1999 | Yang et al. |
| 5,945,319 A | 8/1999 | Keogh |
| 5,977,153 A | 11/1999 | Camiener |
| 5,987,720 A | 11/1999 | Yamamoto |
| 5,993,844 A | 11/1999 | Abraham et al. |
| 6,008,292 A | 12/1999 | Lee et al. |
| 6,017,741 A | 1/2000 | Keogh |
| 6,024,735 A | 2/2000 | Wolfinbarger, Jr. |
| 6,039,726 A | 3/2000 | Lewis et al. |
| 6,063,120 A | 5/2000 | Stone |
| 6,066,160 A | 5/2000 | Colvin et al. |
| 6,086,580 A | 7/2000 | Mordon et al. |
| 6,093,204 A | 7/2000 | Stone |
| 6,093,530 A | 7/2000 | McIlroy et al. |
| 6,106,555 A | 8/2000 | Yang |
| 6,117,979 A | 9/2000 | Hendriks et al. |
| 6,121,041 A | 9/2000 | Mirsch, II et al. |
| 6,126,686 A | 10/2000 | Badylak et al. |
| 6,129,758 A | 10/2000 | Love |
| 6,132,472 A | 10/2000 | Bonutti |
| 6,132,473 A | 10/2000 | Williams et al. |
| 6,132,986 A | 10/2000 | Pathak et al. |
| 6,156,030 A | 12/2000 | Neev |
| 6,156,531 A | 12/2000 | Pathak et al. |
| 6,165,215 A | 12/2000 | Rottenberg et al. |
| 6,166,184 A | 12/2000 | Hendriks et al. |
| 6,174,331 B1 | 1/2001 | Moe et al. |
| 6,177,514 B1 | 1/2001 | Pathak et al. |
| 6,190,407 B1 | 2/2001 | Ogle et al. |
| 6,193,749 B1 | 2/2001 | Schroeder et al. |
| 6,203,755 B1 | 3/2001 | Odland |
| 6,206,873 B1 | 3/2001 | Paolini et al. |
| 6,206,917 B1 | 3/2001 | Williams et al. |
| 6,210,957 B1 | 4/2001 | Carpentier et al. |
| 6,214,054 B1 | 4/2001 | Cunanan et al. |
| 6,214,055 B1 | 4/2001 | Simionescu et al. |
| 6,231,608 B1 | 5/2001 | Stone |
| 6,231,614 B1 | 5/2001 | Yang |
| 6,251,579 B1 | 6/2001 | Moore et al. |
| 6,254,635 B1 | 7/2001 | Schroeder et al. |
| 6,258,320 B1 | 7/2001 | Persing et al. |
| 6,267,786 B1 | 7/2001 | Stone |
| 6,277,555 B1 | 8/2001 | Duran |
| 6,287,338 B1 | 9/2001 | Sarnowski et al. |

(56) References Cited

U.S. PATENT DOCUMENTS

| | | |
|---|---|---|
| 6,290,991 B1 | 9/2001 | Roser et al. |
| 6,293,970 B1 | 9/2001 | Wolfinbarger, Jr. et al. |
| 6,302,909 B1 | 10/2001 | Ogle et al. |
| 6,312,474 B1 | 11/2001 | Francis et al. |
| 6,322,593 B1 | 11/2001 | Pathak et al. |
| 6,322,994 B1 | 11/2001 | Reid |
| 6,328,762 B1 | 12/2001 | Anderson et al. |
| 6,334,873 B1 | 1/2002 | Lane et al. |
| 6,352,708 B1 | 3/2002 | Duran et al. |
| 6,364,905 B1 | 4/2002 | Simpson et al. |
| 6,372,228 B1 | 4/2002 | Gregory |
| 6,375,680 B1 | 4/2002 | Carlyle |
| 6,376,244 B1 | 4/2002 | Atala |
| 6,383,732 B1 | 5/2002 | Stone |
| 6,391,538 B1 | 5/2002 | Vyavahare et al. |
| 6,394,096 B1 | 5/2002 | Constantz |
| 6,448,076 B2 | 9/2002 | Dennis et al. |
| 6,468,660 B2 | 10/2002 | Ogle et al. |
| 6,471,723 B1 | 10/2002 | Ashworth et al. |
| 6,479,079 B1 | 11/2002 | Pathak et al. |
| 6,482,199 B1 | 11/2002 | Neev |
| 6,506,339 B1 | 1/2003 | Giradot et al. |
| 6,509,145 B1 | 1/2003 | Torrianni |
| 6,527,979 B2 | 3/2003 | Constantz et al. |
| 6,528,006 B1 | 3/2003 | Jansen |
| 6,531,310 B1 | 3/2003 | Mirsch, II et al. |
| 6,534,004 B2* | 3/2003 | Chen ............... A01N 1/00 422/1 |
| 6,544,289 B2 | 4/2003 | Wolfinbarger, Jr. et al. |
| 6,547,827 B2 | 4/2003 | Carpentier et al. |
| 6,561,970 B1 | 5/2003 | Carpentier et al. |
| 6,569,200 B2 | 5/2003 | Wolfinbarger, Jr. et al. |
| 6,582,464 B2 | 6/2003 | Gabbay |
| 6,586,006 B2 | 7/2003 | Roser et al. |
| 6,586,573 B1 | 7/2003 | Besman et al. |
| 6,589,591 B1 | 7/2003 | Mansouri |
| 6,605,079 B2 | 8/2003 | Shanks et al. |
| 6,605,667 B1 | 8/2003 | Badejo et al. |
| 6,613,278 B1 | 9/2003 | Mills et al. |
| 6,617,142 B2 | 9/2003 | Keogh et al. |
| 6,630,001 B2 | 10/2003 | Duran et al. |
| 6,652,594 B2 | 11/2003 | Francis et al. |
| 6,653,062 B1 | 11/2003 | DePablo et al. |
| 6,660,265 B1 | 12/2003 | Chen |
| 6,676,654 B1 | 1/2004 | Balle-Petersen et al. |
| 6,676,655 B2 | 1/2004 | McDaniel |
| 6,682,559 B2 | 1/2004 | Myers et al. |
| 6,685,940 B2 | 2/2004 | Andya et al. |
| 6,696,074 B2 | 2/2004 | Dai et al. |
| 6,734,018 B2 | 5/2004 | Wolfinbarger, Jr. et al. |
| 6,753,181 B2 | 6/2004 | Atala |
| 6,790,229 B1 | 9/2004 | Berreklouw |
| 6,797,000 B2 | 9/2004 | Simpson et al. |
| 6,828,310 B2 | 12/2004 | Barresi et al. |
| 6,872,226 B2 | 3/2005 | Cali et al. |
| 6,878,168 B2 | 4/2005 | Carpentier et al. |
| 6,893,666 B2 | 5/2005 | Spievack |
| 6,908,591 B2 | 6/2005 | MacPhee et al. |
| 6,911,043 B2 | 6/2005 | Myers et al. |
| 6,919,172 B2 | 7/2005 | DePablo et al. |
| 6,933,326 B1 | 8/2005 | Griffey et al. |
| 6,939,378 B2 | 9/2005 | Fishman et al. |
| 7,008,763 B2 | 3/2006 | Cheung |
| 7,022,119 B2 | 4/2006 | Hohla |
| 7,037,333 B2 | 5/2006 | Myers et al. |
| 7,063,726 B2 | 6/2006 | Crouch et al. |
| 7,078,163 B2 | 7/2006 | Torrianni |
| 7,087,723 B2 | 8/2006 | Besman et al. |
| 7,141,064 B2 | 11/2006 | Scott et al. |
| 7,143,769 B2 | 12/2006 | Stoltz et al. |
| 7,147,846 B2 | 12/2006 | Anderson et al. |
| 7,176,256 B2 | 2/2007 | Rhee et al. |
| 7,238,200 B2 | 7/2007 | Lee et al. |
| 7,318,998 B2 | 1/2008 | Goldstein et al. |
| 7,338,757 B2 | 3/2008 | Wolfinbarger, Jr. et al. |
| 7,354,749 B2 | 4/2008 | Fisher et al. |
| 7,358,284 B2 | 4/2008 | Griffey et al. |
| 7,367,969 B2 | 5/2008 | Stoltz et al. |
| 7,498,565 B2 | 3/2009 | Silberberg et al. |
| 7,594,974 B2 | 9/2009 | Cali et al. |
| 7,648,676 B2 | 1/2010 | Mills |
| 7,682,304 B2 | 3/2010 | Heyninck-Jantz et al. |
| 7,871,434 B2 | 1/2011 | Case et al. |
| 7,914,569 B2 | 3/2011 | Nguyen et al. |
| 7,919,112 B2 | 4/2011 | Pathak et al. |
| 7,963,958 B2 | 6/2011 | Stoltz et al. |
| 8,007,992 B2 | 8/2011 | Tian et al. |
| 8,043,450 B2 | 10/2011 | Cali et al. |
| 8,075,615 B2 | 12/2011 | Eberhardt et al. |
| 8,136,218 B2 | 3/2012 | Millwee et al. |
| 8,308,797 B2* | 11/2012 | Paniagua ............... A61F 2/2412 623/2.14 |
| 8,357,387 B2* | 1/2013 | Dove ................... A61L 27/3604 424/423 |
| 8,748,490 B2* | 6/2014 | Dove ................... A61L 27/3604 424/423 |
| 2001/0000804 A1 | 5/2001 | Goldstein et al. |
| 2001/0020191 A1 | 9/2001 | Williams et al. |
| 2001/0023372 A1* | 9/2001 | Chen ....................... A01N 1/00 623/23.72 |
| 2001/0025196 A1 | 9/2001 | Chinn et al. |
| 2001/0027344 A1 | 10/2001 | Bonutti |
| 2001/0032024 A1 | 10/2001 | Cunanan et al. |
| 2001/0039459 A1 | 11/2001 | Stone |
| 2002/0001834 A1 | 1/2002 | Keogh et al. |
| 2002/0091441 A1 | 7/2002 | Guzik |
| 2002/0111532 A1 | 8/2002 | Pathak et al. |
| 2002/0120345 A1 | 8/2002 | Wolfinbarger et al. |
| 2003/0027332 A1* | 2/2003 | Lafrance et al. ............. 435/366 |
| 2003/0035843 A1 | 2/2003 | Livesey et al. |
| 2003/0083752 A1 | 5/2003 | Wolfinbarger, Jr. et al. |
| 2003/0125805 A1 | 7/2003 | Johnson et al. |
| 2003/0135284 A1 | 7/2003 | Crouch et al. |
| 2003/0167089 A1 | 9/2003 | Lane |
| 2003/0212454 A1 | 11/2003 | Scott et al. |
| 2003/0217415 A1 | 11/2003 | Crouch et al. |
| 2004/0024452 A1 | 2/2004 | Kruse et al. |
| 2004/0030381 A1 | 2/2004 | Shu |
| 2004/0086543 A1 | 5/2004 | Keogh et al. |
| 2004/0158320 A1 | 8/2004 | Simionescu et al. |
| 2004/0185425 A1 | 9/2004 | Okuda et al. |
| 2004/0193259 A1 | 9/2004 | Gabbay |
| 2005/0010773 A1 | 1/2005 | Lapstun et al. |
| 2005/0079200 A1 | 4/2005 | Rathenow et al. |
| 2005/0113910 A1 | 5/2005 | Paniagua et al. |
| 2005/0119736 A1 | 6/2005 | Zilla et al. |
| 2005/0136510 A1 | 6/2005 | Hendriks et al. |
| 2005/0211680 A1 | 9/2005 | Li et al. |
| 2005/0220848 A1* | 10/2005 | Bates ............................ 424/443 |
| 2005/0246035 A1 | 11/2005 | Wolfinbarger, Jr. et al. |
| 2006/0073592 A1 | 4/2006 | Sun et al. |
| 2006/0084957 A1 | 4/2006 | Delfyett et al. |
| 2006/0099326 A1 | 5/2006 | Keogh et al. |
| 2006/0110370 A1 | 5/2006 | Pathak |
| 2006/0159641 A1 | 7/2006 | Giradot et al. |
| 2006/0177426 A1 | 8/2006 | Gibson et al. |
| 2006/0193885 A1 | 8/2006 | Leonard Neethling et al. |
| 2006/0210960 A1 | 9/2006 | Livesey et al. |
| 2006/0217804 A1 | 9/2006 | Dove |
| 2006/0217805 A1 | 9/2006 | Dove |
| 2006/0228391 A1 | 10/2006 | Seyedin et al. |
| 2006/0259135 A1* | 11/2006 | Navia ................... A61F 2/2409 623/2.11 |
| 2007/0010804 A1 | 1/2007 | Rathjen et al. |
| 2007/0048340 A1 | 3/2007 | Ferren et al. |
| 2007/0050014 A1 | 3/2007 | Johnson |
| 2007/0073392 A1 | 3/2007 | Heyninck-Jantz et al. |
| 2007/0203576 A1 | 8/2007 | Lee et al. |
| 2007/0254005 A1 | 11/2007 | Pathak et al. |
| 2007/0292459 A1 | 12/2007 | Cooper et al. |
| 2008/0195123 A1 | 8/2008 | Gainor et al. |
| 2008/0302372 A1 | 12/2008 | Davidson et al. |
| 2009/0041729 A1 | 2/2009 | Wolfinbarger, Jr. et al. |
| 2009/0112309 A1 | 4/2009 | Jaramillo et al. |

(56) References Cited

U.S. PATENT DOCUMENTS

| | | | |
|---|---|---|---|
| 2009/0118716 | A1 | 5/2009 | Brownell |
| 2009/0130162 | A2 | 5/2009 | Pathak et al. |
| 2009/0137999 | A1 | 5/2009 | Silberberg et al. |
| 2009/0281530 | A1 | 11/2009 | Korn |

FOREIGN PATENT DOCUMENTS

| | | |
|---|---|---|
| WO | 84/01894 A1 | 5/1984 |
| WO | 95/11047 A1 | 4/1995 |
| WO | 95/022361 A1 | 8/1995 |
| WO | 95/034332 A1 | 12/1995 |
| WO | 96/004028 A1 | 2/1996 |
| WO | 96/013227 A1 | 5/1996 |
| WO | 9807452 A1 | 2/1998 |
| WO | WO 98/07452 | 2/1998 |
| WO | 98/43556 A1 | 10/1998 |
| WO | WO 98/43556 | 10/1998 |
| WO | 00/032252 A1 | 6/2000 |
| WO | WO 00/032252 | 6/2000 |
| WO | 02/15948 A2 | 2/2002 |
| WO | WO 02/15948 | 2/2002 |
| WO | 03/037227 A2 | 5/2003 |
| WO | WO 03/037227 | 5/2003 |
| WO | 2004/082536 A1 | 9/2004 |
| WO | WO 04/082536 | 9/2004 |
| WO | 2006/026325 A2 | 3/2006 |
| WO | 2006/099334 A2 | 9/2006 |
| WO | WO 06/099334 | 9/2006 |

OTHER PUBLICATIONS

Dahm, Manfred, et al., "Effects of Surface Seeding with Vital Cells on the Calcium Uptake of Biological Materials for Heart Valve Replacement," J Heart Valve Dis, vol. 5, No. 2, Mar. 1996, 148-151.
Fahner, Peter J., et al., "Systematic Review of Preservation Methods and Clinical Outcome of Infrainguinal Vascular Allografts," The Society for Vascular Surgery, 2006.
Schmidt, Christine E., et al., "Acellular Vascular Tissues: Natural Biomaterials for Tissue Repair and Tissue Engineering," University of Texas at Austin, Department of Chemical Engineering, .2000.
Zilla, P., et al., "Carbodiimide Treatment Dramatically Potentiates the Anticalcific Effect of Alpha-Amino Oleic Acid on Glutaraldehyde-Fixed Aortic Wall Tissue," The Annals of Thoracic Surgery, Elsevier, vol. 79, No. 3, ISSN: 0003-4975; Mar. 1, 2005.
Chvapil et al., "Use of chemically purified and cross-linked bovine pericardium as a ligament substitute", J. Biomed. Mat. Res. 21 (12) :1383-1394 (1987), abstract only.
Al-Fagih et al., "Aortic Valve Repair Using Bovine Pericardium for Cusp Extension", J. Thor. Cardiov. Surg. 96 (5) :760-764 (1988).
Extended European Search Report for corresponding EPO Case No. EP 13 00 1009 dated May 16, 2013.
Carpentier, A., et al., "Biological Factors Affecting Long-Term Results of Valvular Heterografts," Forty-ninth Meeting of the American Association for Thoracic Surgery, San Francisco, CA, Mar. 31-Apr. 2, 1969.
Grant, R.A., et al., "The Effects of Irradiation with High Energy Electrons on the Structure and Reactivity of Native and Cross-Linked Collagen Fibres," J. Cell Sci. vol. 7, 99. 387-405, 1970.
Fumoto, H., et al., "Performance of Bioprosthetic Valves After Glycerol Dehydration, Ethylene Oxide Sterilization, and Rehydration," Innovations, vol. 6, No. 1, Jan./ Feb. 2011.
Hauschka, P., et al., "Direct Identification of the Calcium-Binding Amino Acid, y-Carboxyglutamate, in Mineralized Tissue," Proc. Nat. Acad. Sci, vol. 72, No. 10, pp. 3925-3929, Oct. 1975.
Khor, Eugene, "Methods for the Treatment of Collagenous Tissues for Bioprostheses," Biomaterials, vol. 18, Issue 2, Jan. 1997, pp. 95-105.
Jayakrishnan, A., et al., "Glutaraldehyde as a Fixative in Bioprostheses and Drug Delivery Matrices," Biomaterials, vol. 17, Issue 5, 1996, pp. 471-484.
Olde Damink, L.H.H., et al., "Influence of Ethylene Oxide Gas Treatment on the in vitro Degradation Behavior of dermal Sheep Collagen," Journal of Biomedical Materials Resarch, vol. 29, pp. 149-155, 1995.
Ohan, M., et al., "Glucose Stabilizes Collagen Sterilized with Gamma Irradiation," Wiley Periodicals, Inc., pp. 1188-1195, 2003.
R Parker, et al. Storage of Heart Valve Allografts in Glycerol With Subsequent Antibiotic Sterilisation, Thorax, 1978, 538-645, vol. 33:5, British Thoracic Society, London, UK.
Saegeman, V., et al., "Short and long term bacterial inhibiting effect of high concentrations of glycerol used in the prevention of skin allografts," Science Direct, Burns, No. 34, Mar. 2008.
S. Chauvaud et al., "Valve Extension with Glutaraldehyde-Preserved Autologous Pericardium. Results in Mitral Valve Repair", 1991, J Thorac Cardiovasc Surg., vol. 102(2), pp. 171-177 (abstract only).

\* cited by examiner

BIOLOGICAL TISSUE FOR SURGICAL IMPLANTATION

RELATED APPLICATION

The present application is a divisional of U.S. application Ser. No. 11/877,548, filed Oct. 23, 2007 now U.S. Pat. No. 8,007,992 which claims priority under 35 U.S.C. § 119(e) to U.S. Provisional Application No. 60/854,938, filed Oct. 27, 2006.

FIELD OF INVENTION

The invention is directed to the preparation or storage of biological tissues used for surgical implantation. The invention is also directed to biological tissues and bioprosthetic devices containing such tissues.

BACKGROUND OF THE INVENTION

Animal tissue that is often used in implantable bioprosthetic devices or to repair damaged tissue in a patient is typically provided to medical personnel stored with or previously treated with chemical agents such as formaldehyde and/or glutaraldehyde. This chemical treatment helps to prevent rejection of the implanted bioprosthetic device by the recipient, provides for sterilization and helps to stabilize the proteins in the tissue, thereby making the tissue or device containing such tissue more resistant to mechanical fatigue and degradation by proteolytic enzymes. Formaldehyde and glutaraldehyde, for example, stabilize the tissue by forming cross-links with collagen and other proteins in the tissue. Also, the tissue is often stored in a dilute aqueous solution containing glutaraldehyde (and/or formaldehyde) to maintain the tissue components in a hydrated state and to maintain a microbe-free environment. However, tissue containing these agents must be extensively rinsed prior to surgical implantation. Moreover, an important consideration in selecting a biological tissue for implantation is that the tissue should be readily available to medical personnel in as close to a ready-to-use form as possible, that is, with minimal preparation prior to surgery. This reduces the opportunities for error and also the implantation time.

Attempts have been made to develop procedures to pretreat biological tissue and bioprosthetic devices containing biological tissue so that such tissue and devices can be provided to medical personnel substantially free of formaldehyde or glutaraldehyde, and to provide the biological tissue in a substantially dry form that is ready for implantation or rehydration. One attempt to address this issue involved immersing the biological tissue in aqueous $C_1$-$C_3$ alcohol, for example aqueous ethanol solutions, see, U.S. Pat. Nos. 6,277,555 and 6,630,001 to Duran et al. The solution treated tissue is then immersed in an aqueous glycerol solution or low molecular weight (<1000 D) polyethylene glycol. Thereafter, the tissue is briefly immersed in aqueous heparin solution, frozen and lyophilized.

U.S. Pat. No. 4,300,243 describes the preparation of biological collagenous tissue for surgical implantation. The preparation of the tissue includes contacting the tissue with fresh amounts of a water-miscible organic solvent selected from the group consisting of methanol, ethanol, propanol, isopropanol, acetone, methylethylketone and mixtures thereof. The excess alcohol is then removed at a pressure of between 0.1 bar to 1.0 bar. However, it is known that such dehydration processes significantly reduce the overall dimensions of the tissue, that is, the tissue shrinks. Also, biological tissue subject to this dehydration process cannot be successfully rehydrated and returned to substantially its original dimensions. As a result, bioprosthetic devices comprising tissue components that have undergone such a dehydration process are not good candidates for implantation. See, U.S. Pat. No. 6,534,004, col. 1, lines 53-65.

U.S. Pat. No. 6,534,004 describes a process of providing bioprosthetic devices containing a biological tissue for dry storage. The process includes treating the biological tissue with an aqueous solution of organic compounds having a plurality of hydroxyl groups (e.g., polyhydric alcohols, polyglycols or water soluble carbohydrates). One of the more preferred treatment solutions is an aqueous solution of glycerol or derivatives of glycerol. The biological tissue is immersed in this solution, removed and permitted to dry in air. The tissue is then sterilized and packaged for storage.

All the foregoing prior art approaches to preparing tissue for dry storage require the use of aqueous solutions. However, the use of aqueous solutions makes the tissue susceptible to microbial contamination. It is desirable, therefore, to totally eliminate water from the process and to thus render the dried tissue less prone to microbes. The present invention provides such a process. It provides new methods for preparing biological tissue or bioprosthetic devices containing such tissue suitable for sterile dry storage, and available to medical personnel in as close to ready-to-use form as possible.

SUMMARY OF THE INVENTION

A method of treating a biological tissue that enables dry storage of said tissue is disclosed. In one embodiment, the method comprises contacting the biological tissue with a non-aqueous treatment solution comprising a polyhydric alcohol and a $C_1$-$C_3$ alcohol and removing a portion of the treatment solution from the solution-treated biological tissue. The polyhydric alcohol concentration can be 40-95% and the $C_1$-$C_3$ alcohol concentration can be 5-60% by volume. The time of contact between the tissue and treatment solution can be varied to control the treatment process. For example, in some embodiments, the step of contacting the biological tissue with the treatment solution is performed for a time of greater than 30 minutes.

In some embodiment, the polyhydric alcohol is glycerol and the $C_1$-$C_3$ alcohol is selected from the group consisting of ethanol, n-propanol, 2-propanol or a mixture thereof.

The biological tissue to be treated can be mammalian tissue, for example, a tissue selected from the group consisting of pericardium, aortic and pulmonary roots and valves, tendons, ligaments, skin, dura, peritonium, blood vessels, pleura, diameter, mitral and tricuspid valves.

In one embodiment, the treatment method further comprises placing the biological tissue ready for sterilized containment in a package form, wherein the package form is pre-sterilized or sterilized following the placement of the tissue in the package form, and sealing the package form.

Also disclosed herein is a sealed package containing a sterilized solution-treated, biological tissue for surgical implantation into a human, wherein the solution-treated, biological tissue is prepared by one of the embodiments of the above-described treatment process. Further, a sterilized solution-treated, biological tissue for surgical implantation into a human is disclosed wherein the sterilized, solution-treated biological tissue prepared by one of the embodiments of the above-described treatment process. Also disclosed is a heart valve prosthesis that comprises a collapsible, elastic valve member, wherein the valve member comprises a biological tissue that is solution-treated, using one of the embodiments of the above-described treatment process, an elastic stent member in which the valve member is mounted, the stent member having internal and external surfaces and a support coupled to the valve member and positioned between the valve member and the stent member, wherein the stent member forms a continuous surface and comprises strut members that provide a structure sufficiently rigid to prevent eversion, and the support extends from the internal surface of the stent member to the external surface of the stent member, and wherein the stent member has sufficient radial and longitudinal rigidity to withstand the radial force necessary for implantation, to resist aortic recoil forces, and to provide long-term support to the valve prosthesis. In one embodiment, the heart valve prosthesis is provided in sterilized form and ready for surgical implantation.

DETAILED DESCRIPTION OF THE DRAWING

No figures are provided.

DETAILED DESCRIPTION OF THE INVENTION

The invention is directed to a method of treating a biological tissue of a mammal for preparation or storage. Ideally, the method provides biological tissue or bioprosthetic devices containing such tissue ready for surgical implantation, or for rehydration, e.g., with physiologic saline. One embodiment of the invention utilizes a non-aqueous combination of a polyhydric alcohol and a $C_1$-$C_3$ alcohol. The method comprises contacting the biological tissue with a treatment solution comprising greater than 35% by volume of a polyhydric alcohol and the balance of a $C_1$-$C_3$ alcohol. The treatment solution contains no water, i.e., it is non-aqueous. For tissue that is stored in a sterile storage solution for example a fixative solution, contact of the biological tissue with the treatment solution, e.g., by immersing the tissue in the solution, is maintained for a time sufficient to exchange a substantial portion of the pre-storage fluid, which may be aqueous, within the interstitial volume of the tissue with the treatment solution. The method also includes removing a portion of the treatment solution from the solution-treated tissue to provide a biological tissue ready for sterilized containment.

As used herein, a "polyhydric alcohol" is an organic molecule that contains a plurality of carbon atoms and two or more hydroxyl groups, wherein the hydroxyl groups are attached to carbon atoms. Exemplary polyhydric alcohols include glycerol, ethylene glycol, polyethylene glycols, propylene glycol, butylene glycol and derivatives of glycerol. Two of the more preferred polyhydric alcohols used in the process are glycerol and propylene glycol, and derivatives of glycerol or propylene glycol. Of course, one or more polyhydric alcohols in the form of a mixture can be used in the process. Thus, it is to be understood that the term "a polyhydric alcohol" is inclusive of a mixture of two or more polyhydric alcohols. For example, a mixture of glycerol and propylene glycol can be used in the process.

The biological tissue used in various embodiments of the invention can be mammalian tissue, including human tissue, such as tissue obtained from human donors or cadavers. Bovine, ovine, equine, and porcine tissue can also be used. The types of tissue used in these embodiments is the same tissue used in common surgical procedures, and includes pericardium, aortic and pulmonary roots and valves, tendons, ligaments, skin, peritoneum, facia, pleura, mitral and tricuspid valves.

One of ordinary skill in the art would understand that the treatment processes in accordance with some embodiments of the invention can be practiced with fixed tissue or native tissue. In some instances the biological tissue used in the process has been previously fixed by treating the tissue with a fixative solution. As used herein "fixed" tissue is one in which the proteins thereof have reduced solubility, antigenicity, and biodegrading properties as compared to the proteins in the native tissue. Typically, the tissue is fixed by cross-linking the amine groups of the proteins of the tissue with an aldehyde. The tissue fixation process can include chemical and/or enzyme decellularization steps. The fixed tissue is rinsed to substantially reduce the amount of unreacted fixative within the tissue. In other instances, the biological tissue is temporarily stored in a buffered saline solution prior to the inventive treatment disclosed in this application.

The biological tissue is contacted with a treatment solution, e.g., by immersing the tissue in the solution. In some embodiments, the volume of the treatment solution is at least two times, at least fifty times or at least one hundred times, the volume of the biological tissue that is brought into contact with the solution. If the biological tissue is to be attached to a bioprosthetic device for implantation, the tissue can be treated with the treatment solution prior to its attachment or after its attachment to the bioprosthetic device. For example, bovine pericardium can be treated with the treatment solution prior to the time it is formed into a heart valve, vascular graft, stent covering, or pericardial patch or after the bovine pericardium is formed into a heart valve, vascular graft, stent covering, or pericardial patch.

The $C_1$-$C_3$ alcohol is selected from the group consisting of methanol, ethanol, isopropanol and n-propanol. Ethanol is the preferred alcohol used in the process. Again, it is to be understood that the term "a $C_1$-$C_3$ alcohol" is inclusive of a mixture of two or more $C_1$-$C_3$ alcohols. For example, a mixture of ethanol and isopropanol can be used in the process.

The inventors have discovered that the concentration of the polyhydric alcohol relative to the $C_1$-$C_3$ alcohol affects the dimensional stability of the biological tissue during storage. One other factor related to the dimensional stability of the tissue is the type of tissue itself. For some biological tissue, the treatment solution will comprise 70% to 95% by volume of a polyhydric alcohol and 5% to 30% by volume of a $C_1$-$C_3$ alcohol. For example, applicants have determined that for bovine pericardium heart valve the treatment solution will preferably comprise 70% to 95% by volume of a polyhydric alcohol, and 5% to 30% by volume of a $C_1$-$C_3$ alcohol.

For tissue stored in a storage solution or fixative, by contacting the biological tissue with the non-aqueous treatment solution water is removed from the interstitial volume of the tissue, rendering the tissue substantially dry.

Those skilled in the art will readily recognize that the biological tissue can be contacted with the treatment solution in one or more separate contacting steps. Instead of contacting the tissue with the treatment solution in a single treatment step, the contact step can be repeated one or more times using treatment solutions of the same or similar concentrations of polyhydric alcohol and $C_1$-$C_3$ alcohol. For example, two immersion baths containing the same treatment solutions can be arranged. The biological tissue containing a pre-storage fluid is immersed in the first bath for a first time period. The tissue is then removed from the first bath and immersed in the second bath for a second time period. Of course, one of ordinary skill may determine that the respective concentrations of the polyhydric alcohol and the $C_1$-$C_3$ alcohol in each of the two baths are different, yet within the stated and claimed amounts.

The time of contact between the biological tissue and the treatment solutions is somewhat dependent on the thickness and type of the tissue. As can be expected, with a relatively thick tissue more time of contact is typically needed. Additionally, as is well-known to a person of ordinary skill in the art, process variables such as agitation, temperature, pressure, flow rate, etc., will affect the needed time of contact.

The preparation of a polyhydric alcohol and C1-C3 alcohol mixture (for example, a 75%-25% mixture) can take several hours with stirring. The time needed to treat tissue with this solution depends on many factors above mentioned and can take up to several hours. In many cases, the process will involve maintaining biological tissue with the treatment solution for eight hours or more. In some instances, the time of exposure can exceed twelve, sixteen or twenty-four hours.

Once the biological tissue has been sufficiently exposed to the treatment solution, the tissue is removed from the solution and exposed to ambient air or an inert environment, e.g., nitrogen, at standard room temperature and humidity so as not to adversely affect tissue properties (typically, at a temperature from about 15° C. to about 25° C., and relative humidity preferably less than about 50%). Preferably, the drying is performed in a clean room or in a laminar flow bench at ambient room conditions for about 1-4 hours.

The treated and dried tissue or a bioprosthetic device containing the treated and dried tissue is then packaged in a container or package essentially free of liquid for subsequent rehydration or implantation. A container or package that is "essentially free of liquid" means a non-fluid environment in which the presence of water or other substances is limited to approximately the content of such substances in ambient air (as more precisely defined by the relative humidity). The tissue or the bioprosthetic device containing the tissue is placed into a micro-organism resistant container or package. One preferred method is to apply a vacuum to the package to minimize the level of $O_2$, and may additionally utilize a backfill of an inert gas, such as nitrogen. Such methods of sterile packaging are known to those skilled in the art. The packaged treated tissue can then be sterilized by a gaseous sterilization process or by an exposure to ionizing radiation including standard gamma and E-Beam methods. To ensure that the chamber remains sterile following sterilization, the package members are formed from a material that is impenetrable to micro-organisms such as bacteria and fungi. After the tissue or bioprosthetic device containing such tissue is placed in the chamber and/or sterilized, the chamber is sealed.

Sterilization by exposure to ionizing radiation or sterilizing gas, particularly by exposure to ethylene oxide, is within the skill of the art. In a preferred embodiment, the tissue is sterilized by exposing the tissue to gamma radiation. Examples of conventional procedures for sterilization by exposure to ethylene oxide involve exposure to 10% ethylene oxide and 90% hydrochlorofluorocarbon at a chamber pressure of 8 to 10 psig at a temperature of 38° C. for 24 hours or at a temperature of 54-57° C. for 130 minutes.

The resulting product is a substantially sterile and sealed implantable tissue or bioprosthetic device containing such tissue present in a substantially dry form. It is especially well-suited for surgical implantation into human patients for the treatment of any number of diseases or conditions. Prior to surgical implantation, the biological tissue or bioprosthetic device containing such tissue is removed from the package, and the tissue component optionally rehydrated by exposure to an aqueous solution, preferably a sterile aqueous solution. The tissue can be rehydrated by multiple soakings in a sterile solution such as physiologic saline. The glycerol in the tissue can be easily washed off by saline. The majority of glycerol is eluted out by washing the tissue in saline for about 3-5 minutes.

The described method of treating biological tissue and the subsequent packaging of the tissue or device containing such tissue eliminates the need to sterilize the tissue or the bioprosthetic devices by medical personnel prior to surgical implantation. The described method provides greater manufacturing control in preparing tissue and bioprosthetic devices for surgical implantation. In other words, the process of preparing the tissue or prosthetic device for implantation need not occur at the hospital or in the operating room. Again, the only step that may be required of medical personnel is to rehydrate the tissue, or the tissue on the bioprosthetic device, with physiologic saline or other suitable rehydrating agents.

The described method provides a biological tissue or bioprosthetic devices containing such tissue with dimensional stability that is essentially ready for surgical implantation into a patient. Biological tissue treated in accordance with the methods described and claimed in this application will typically return to a size that is at least about 97%, more preferably at least about 99% of its original hydrated size following dry storage for about 24 hours and rehydration in physiologic saline for about 5 minutes. Accordingly, biological tissue prepared in accordance with the described and claimed method are well-suited for use in an implantable bioprosthetic device, and in particular, a blood-contacting bioprosthetic device that is implanted into the cardiovascular system of a patient.

An embodiment of the invention is also directed to a bioprosthetic device that includes a pericardium tissue heart valve processed by the methods described in this application. As mentioned, the pericardium tissue can be processed according to the described methods prior to or following its attachment to the device. The heart valve has multiple leaflets joined together at a periphery of the valve at valve commissures (a portion of the holder) that are generally axially aligned and evenly disposed about a valve axis. The valve commissures are each disposed between adjacent curvilinear valve cusps along the periphery of the valve. The bioprosthetic heart valve may further include a holder that comprises a plurality of cusp supports arranged around an axis to contact the heart valve generally along the valve cusps. The pericardium heart valve attached to the holder is prepared and treated by the method described in this application. A more complete description of a bioprosthetic heart valve is described in U.S. Pat. No. 5,928,281, which is assigned to Edwards Lifesciences, the entire disclosure of which is incorporated into this application by reference.

Example 1

Bovine pericardium fixed in the presence of glutaraldehyde is dissected to remove loose tissue and fat and sliced into discs having a thickness and diameter as noted in Tables 1 and 2. The dimensions of each disc are measured prior to treatment, and each of the discs is immersed in the various treatment solution compositions reported in Tables 1 and 2. The treatment solutions are prepared approximately 16 hours prior to use of the solutions. The tissue is immersed in each of the various solution compositions at a solution: tissue volume ratio of 100:1. The tissue maintains contact with the various treatment solutions for approximately 16 hours, after which the tissue is carefully removed from the solution, excess liquid is allowed to drain from the tissue and the tissue dried by air. The dimensions of each of the discs are again measured. After 16 hours in the dried form, each of the discs is rehydrated in normal saline. The rehydrated dimensions are again measured.

TABLE 1

| Composition | 1 | 2 | 3 | 4 | 5 | 6 | 7 | 8 |
|---|---|---|---|---|---|---|---|---|
| Glycerol (%) | 100 | 90 | 80 | 70 | 60 | 50 | 40 | 30 |
| Ethanol (%) | 0 | 10 | 20 | 30 | 40 | 50 | 60 | 70 |
| Tissue disc diameter (mm) (Mean ± SD) | | | | | | | | |
| Before Treatment | 8.12 ± 0.06 | 8.26 ± 0.11 | 8.14 ± 0.07 | 8.14 ± 0.10 | 8.14 ± 0.08 | 8.20 ± 0.16 | 8.23 ± 0.11 | 8.2 ± 0.09 |
| Treated Dehydrated | 8.06 ± 0.04 | 8.12 ± 0.07 | 8.00 ± 0.05 | 8.02 ± 0.02 | 7.93 ± 0.03 | 7.81 ± 0.11 | 7.66 ± 0.09 | 7.25 ± 0.35 |
| Treated Rehydrated | 8.20 ± 0.23 | 8.23 ± 0.07 | 8.12 ± 0.06 | 8.14 ± 0.10 | 8.10 ± 0.10 | 8.11 ± 0.18 | 8.01 ± 0.11 | 7.89 ± 0.15 |

TABLE 2

| Composition | 1 | 2 | 3 | 4 | 5 | 6 | 7 | 8 |
|---|---|---|---|---|---|---|---|---|
| Glycerol (%) | 100 | 90 | 80 | 70 | 60 | 50 | 40 | 30 |
| Ethanol (%) | 0 | 10 | 20 | 30 | 40 | 50 | 60 | 70 |
| Tissue thickness (mm) (Mean ± SD) | | | | | | | | |
| Before Treatment | 0.34 ± 0.02 | 0.36 ± 0.02 | 0.34 ± 0.05 | 0.38 ± 0.04 | 0.34 ± 0.05 | 0.34 ± 0.03 | 0.35 ± 0.06 | 0.38 ± 0.06 |
| Glycerol Treated Dehydrated | 0.39 ± 0.04 | 0.36 ± 0.06 | 0.37 ± 0.06 | 0.38 ± 0.04 | 0.34 ± 0.07 | 0.34 ± 0.05 | 0.32 ± 0.04 | 0.32 ± 0.07 |
| Glycerol Treated Rehydrated | 0.35 ± 0.03 | 0.33 ± 0.05 | 0.34 ± 0.04 | 0.38 ± 0.04 | 0.34 ± 0.05 | 0.34 ± 0.04 | 0.32 ± 0.05 | 0.33 ± 0.06 |

The treated and dried tissue is pliable and does not crack or break by physical manipulations. It is rehydrated by immersion in, for example, physiological buffered saline for approximately 5 minutes at ambient temperature. After rehydration, the tissue is indistinguishable in appearance from the original (untreated) fixed tissue.

As shown by the data of Tables 1 and 2, the tissue maintains dimensional stability for all ranges of composition evaluated. However, for more critical dimensional, considerations, e.g. bioprosthetic heart valves, treatment solution compositional ranges between about 50 to 95% glycerol, and the balance alcohol are preferred.

Similar results were obtained from measurements of tissue thickness following rehydration. In this case, there was no observed difference in tissue thickness for those disks treated with a solution at a volume ratio of glycerol: ethanol from 80:20 to 50:50.

Although various preferred embodiments of the present invention have been disclosed for illustrative purposes, those skilled in the art will appreciate that various modifications, additions and/or substitutions are possible without departing from the scope and spirit of the present invention as disclosed in the claims.

We claim:

1. A sealed package containing a sterilized bioprosthesis comprising:

a bioprosthetic heart valve comprising a pliable, elastic, and glutaraldehyde-fixed biological tissue having an interstitial volume comprising glycerol, wherein the biological tissue is coupled to a stent and wherein the bioprosthetic heart valve is treated with a solution comprising 50-90% glycerol and 50-10% ethanol; and the sealed package containing the bioprosthetic heart valve, wherein the sealed package does not contain a liquid storage solution in contact with the bioprosthetic heart valve.

2. The sealed package of claim 1, wherein the biological tissue is selected from the group consisting of pericardium, aortic and pulmonary roots, tendons, ligaments, skin, facia, peritonium, pleura, and mitral and tricuspid valves.

3. The sealed package of claim 1, wherein the biological tissue is decellularized.

4. The sealed package of claim 1, wherein the stent is elastic and the bioprosthetic heart valve is collapsible.

5. The sealed package of claim 1, wherein the sealed package is sterilized by a gas or by exposure to ionizing radiation.

6. The sealed package of claim 5, wherein the gas is ethylene oxide.

* * * * *